(12) United States Patent
Gonzalez et al.

(10) Patent No.: US 11,714,039 B2
(45) Date of Patent: Aug. 1, 2023

(54) DEVICE AND METHOD TO OBTAIN THE VISCOSITY OF POLYMER FLUIDS USED FOR ENHANCED OIL RECOVERY

(71) Applicant: SAUDI ARABIAN OIL COMPANY, Dhahran (SA)

(72) Inventors: Miguel Gonzalez, Houston, TX (US); Subhash Chandrabose Ayirala, Dhahran (SA); Lyla Maskeen, Dammam (SA); Abdulkarim Sofi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 182 days.

(21) Appl. No.: 17/091,402

(22) Filed: Nov. 6, 2020

(65) Prior Publication Data
US 2022/0146393 A1 May 12, 2022

(51) Int. Cl.
*G01N 11/16* (2006.01)
*G01N 33/44* (2006.01)
*G01N 11/00* (2006.01)

(52) U.S. Cl.
CPC .......... *G01N 11/16* (2013.01); *G01N 33/442* (2013.01); *G01N 2011/0006* (2013.01); *G01N 2011/0026* (2013.01); *G01N 2011/0046* (2013.01)

(58) Field of Classification Search
None
See application file for complete search history.

(56) References Cited

U.S. PATENT DOCUMENTS

| 5,235,844 A | 8/1993 | Bonne et al. |
| 5,798,452 A | 8/1998 | Martin et al. |
| 6,141,625 A | 10/2000 | Smith et al. |

(Continued)

FOREIGN PATENT DOCUMENTS

| JP | 2534173 B2 | 9/1996 |
| JP | 2007336045 A | 12/2007 |
| WO | 2014/049698 A1 | 4/2014 |

OTHER PUBLICATIONS

Zhang M, Chen D, He X, Wang X. A Hydrodynamic Model for Measuring Fluid Density and Viscosity by Using Quartz Tuning Forks. Sensors (Basel). Dec. 29, 2019;20(1):198. doi: 10.3390/s20010198. PMID: 31905800; PMCID: PMC6982936. (Year: 2019).*

(Continued)

*Primary Examiner* — Paul M. West
*Assistant Examiner* — Mark A Shabman
(74) *Attorney, Agent, or Firm* — Osha Bergman Watanabe & Burton LLP (57) ABSTRACT

An apparatus for measuring a viscosity of a fluid is disclosed. The apparatus includes a Parylene coated quartz tuning fork for immersion in the fluid and an electronic circuit to excite a vibration of the Parylene coated quartz tuning fork and measure one or more vibrational parameters of the Parylene coated quartz tuning fork. A computer processor is configured to determine a non-Newtonian viscosity from the vibration of the Parylene coated quartz tuning fork based, at least in part, on a Stokes flow hydrodynamic model. The computer processor is coupled to a memory for storing a calibration curve to determine a Newtonian viscosity of the fluid from the non-Newtonian viscosity of the fluid.

7 Claims, 9 Drawing Sheets

(56) References Cited

U.S. PATENT DOCUMENTS

| | | | |
|---|---|---|---|
| 2002/0178805 | A1 | 12/2002 | DiFoggio et al. |
| 2005/0247119 | A1* | 11/2005 | DiFoggio ............... G01N 33/24 73/152.47 |
| 2008/0215245 | A1 | 9/2008 | Reittinger |
| 2010/0324852 | A1* | 12/2010 | Wolf ...................... G01H 13/00 702/104 |
| 2013/0139576 | A1 | 6/2013 | Goodbread et al. |
| 2019/0293825 | A1 | 9/2019 | Gonzalez et al. |
| 2019/0332089 | A1 | 10/2019 | Deffenbaugh et al. |
| 2020/0149395 | A1 | 5/2020 | Bouldin et al. |

OTHER PUBLICATIONS

International Search Report and Written Opinion issued in Application No. PCT/US2021/058292, dated Feb. 22, 2022 (17 pages).
L. Matsiev; "Measurements of Liquid Density and Viscosity with Flexural Resonators Using Noise as an Excavation Source", 2006 IEEE Ultrasonics Symposium; Oct. 2, 2006; pp. 884-887 (4 pages).
Gonzalez, M. et al.; "Electromechanical Tuning Fork Resonator For Drilling Fluid Viscometry and Densitometry", 2019 IEEE Sensors, Oct. 2019; pp. 1-4 (4 pages).
"Fluid Sensing Using Quartz Tuning Forks-measurement Technology and Applications", Voglhuber-Brunnmaier, T et al., Source: Published In: Sensors 19(10): 2336. Publication Date: May 21, 2019 (15 pages).
Melo, Maria de, and Elizabete Lucas. "Characterization and Selection of Polymers for Future Research on Enhanced Oil Recovery", Chemistry & Chemical Technology vol. 2, No. 4, 2008 (9 pages).
Dupas, A., I. Hénaut, J.-F. Argillier, and T. Aubry. "Mechanical Degradation Onset of Polyethylene Oxide Used as a Hydrosoluble Model Polymer for Enhanced Oil Recovery." Oil & Gas Science and Technology—Revue d'IFP Energies Nouvelles 67, No. 6 (Nov. 2012) (10 pages).
Blaauwgeers, R., Blazkova, M., Clovecko, M., Eltsov, V.B., de Graaf, R., Hosio, J., Krusius, M., Schmoranzer, D., Schoepe, W., Skrbek, L., Skyba, P., Solntsev, R.E., Zmeev, D.E., 2007, March. "Quartz Tuning Fork: Thermometer, Pressure—and Viscometer for Helium Liquids." J. of Low Temperature Physics; 146(5-6), (pp. 537-562) (27 pages).
Seder, J.E., 1998, "Frequency response of cantilever beams immersed in viscous fluids with applications to the atomic force microscope" J. Applied Physics; 84(1), pp. 64-76 (13 pages).
Gonzalez, M., Seren, H.R., Ham, G., Buzi, E., Bemero, G. and Deffenbaugh, M., 2017. "Viscosity and density measurements using mechanical oscillators in oil and gas applications" IEEE Transactions on Instrumentation and Measurement, 67(4), pp. 804-810 (7 pages).
https://www.rheosense.com/products/extensional-viscometer/e-vroc/overview (1 page) Retrieved Nov. 5, 2020.

* cited by examiner

DEVICE AND METHOD TO OBTAIN THE VISCOSITY OF POLYMER FLUIDS USED FOR ENHANCED OIL RECOVERY

BACKGROUND

Hydrocarbon fluids are often found in hydrocarbon reservoirs located in porous rock formations far below the earth's surface. Production wells may be drilled to extract the hydrocarbon fluids from the hydrocarbon reservoirs. Injection wells may be drilled into the same reservoirs through which fluids may be pumped to maintain, or increase, reservoir pressure, and sweep hydrocarbon fluids through the hydrocarbon reservoir to the production wells, thereby facilitating production. This process of sweeping the hydrocarbon fluid to the production wells will henceforth be called enhanced oil recovery.

The value of viscosity of the injection fluid is an important factor in the efficiency of enhanced oil recovery, and polymers may be added to a base fluid, such as water, to achieve the desired viscosity. The viscosity of the mixture may be measured in a laboratory using a calibrated rheometer. However, during the injection process, the added polymers may suffer from degradation due to mechanical and chemical changes experienced before and during pumping. Thus, the values measured in the laboratory may not be representative of the true viscosity of the fluid mixture when it enters the well head or the reservoir. Consequently, a compact viscometer that may measure the viscosity of the mixture in situ and is suitable for well head or downhole deployment is desirable.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

The present disclosure presents, in one or more embodiments, an apparatus, a method of calibration for the apparatus, and a method of use for the apparatus to measure a viscosity of a fluid. In general, and in one embodiment, the apparatus includes a Parylene coated quartz tuning fork for immersion in the fluid. The apparatus further includes an electronic circuit to excite a vibration of the Parylene coated quartz tuning fork and measure one or more vibrational parameters of the Parylene coated quartz tuning fork. A computer processor is configured to determine a non-Newtonian viscosity from the vibration of the Parylene coated quartz tuning fork based, at least in part, on a Stokes flow hydrodynamic model. The computer processor is coupled to a memory for storing a calibration curve to determine a Newtonian viscosity from the non-Newtonian viscosity.

In some embodiments, a method for calibrating the apparatus to measure the non-Newtonian viscosity of a non-Newtonian fluid includes measuring, at a plurality of frequencies, a vibrational response of a Parylene coated quartz tuning fork immersed in a Newtonian fluid. The vibrational response of the Parylene coated quartz tuning fork is fit to a resonance peak using a transfer function. One or more Newtonian viscosities is determined from the transfer function and a stokes hydrodynamic model. The non-Newtonian viscosity for a plurality of non-Newtonian calibration fluids at a plurality of fluid shear rates is obtained, and a Newtonian viscosity of the non-Newtonian calibration fluids is measured at a plurality of frequencies using the Parylene coated quartz tuning fork. The Newtonian viscosity is plotted against the non-Newtonian viscosity and a calibration curve is fit to the data points so the apparatus may measure the non-Newtonian viscosity of a non-Newtonian fluid.

In further embodiments, a method for utilizing the apparatus to measure the viscosity of a fluid includes inserting the Parylene coated quartz tuning fork into a non-Newtonian fluid and exciting a vibration using a generator. The vibration parameters relate to a Newtonian viscosity through a transfer function and a Stokes hydrodynamic model. Using a calibration curve, generated by a calibration method, and the Newtonian viscosity, a non-Newtonian viscosity of the non-Newtonian fluid may be measured and recorded.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Polymer additives are used across different fields to tune the viscous and/or rheological properties of fluids in order to optimize industrial processes. For example, during enhanced oil recovery (EOR) polymers are added to increase the viscosity of the injected water in order to have a more favorable oil displacement at the reservoir, thus increasing recovery rates and oil production. Quality control of the injected fluids is crucial to a successful operation in order to avoid and/or detect degradation of the fluids. To this end, embodiments disclosed herein relate to a compact viscometer for field/downhole deployment that is able to verify the targeted viscosity values and is cost efficient. Such a viscometer has a significant impact on EOR by providing accurate QA/QC evaluations on the injected polymer fluids.

Figure 1:
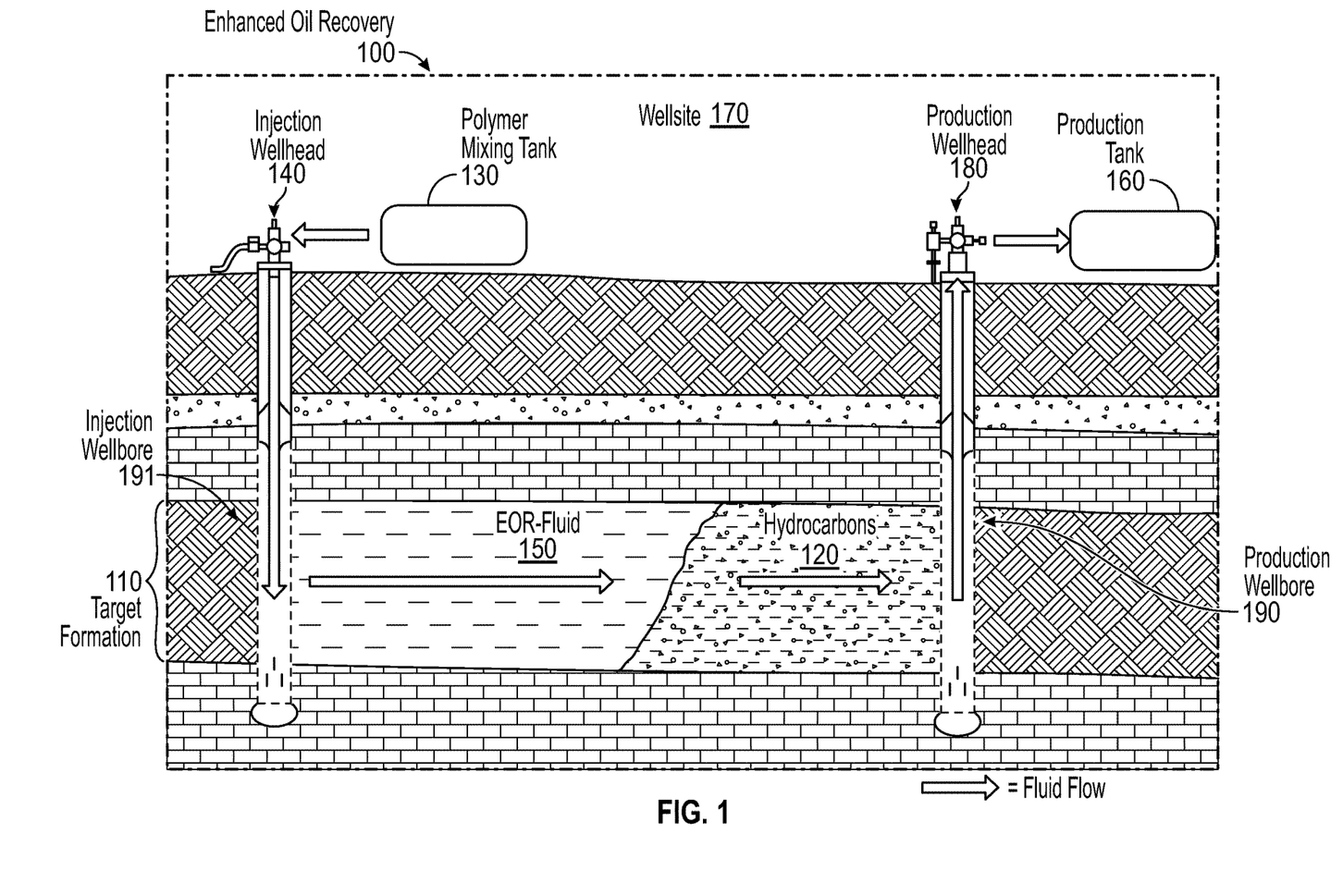
FIG. 1 shows fluid flow and major physical components of enhanced oil recovery in accordance with one or more embodiments.

FIG. 1 depicts a cross sectional schematic view of an example of an active EOR operation (100) occurring in a target formation (110) originally saturated with hydrocarbons (120). In an EOR (100) operation, a base fluid such as water may be mixed with an additive such as a polymer to form an enhanced oil recovery fluid. This enhanced oil recovery fluid will, herein, be denoted as an "EOR-fluid" (150). In one or more embodiments, the base fluid and the polymers may be mixed in a polymer mixing tank (130). In other embodiments, polymers may be added directly to the base fluid in a base fluid tank. In further embodiments, the mixing of the base fluid and polymers may occur as the fluid is being pumped into the injection wellhead (140) or prior to arrival of the base fluid and polymer at the wellsite (170).

Once the EOR-fluid (150) is prepared, the EOR-fluid (150) may be injected into the target formation (110) through one or more injection wellheads (140). This EOR-fluid (150) helps to maintain or increase the pressure of the target formation (100) to facilitate the recovery of the hydrocarbons (120) to one or more production wellheads (180) into one or more production tanks (160). Hydrocarbons may also flow from the production wellhead (180) directly into a pipeline or separation tanks. The injection of the EOR-fluid (150) may sweep, or push, hydrocarbons (120) to the production wellbore (190).

The base fluid may be mixed with polymers to form an EOR-fluid (150) with chemical and mechanical properties favorable for the EOR (100) operation. In some cases, the base fluid may be water and the polymers may be added to increase the viscosity and density of the water to a favorable value. In some EOR (100) operations, the base fluid may not need to be mixed with anything as the base fluid's mechanical and chemical values may already match the required values. These required values are important in ensuring that the EOR-fluid (150) may fully saturate the target formation (110) and optimally recover, or sweep, the hydrocarbons (120) to the production wellbore (190). Thus, a means of measuring fluid properties, such as viscosity, at the polymer mixing tank (130) may be desirable. In other embodiments, a means of measuring fluid properties downhole, in the injection wellbore (191), may be desirable.

Figure 2:
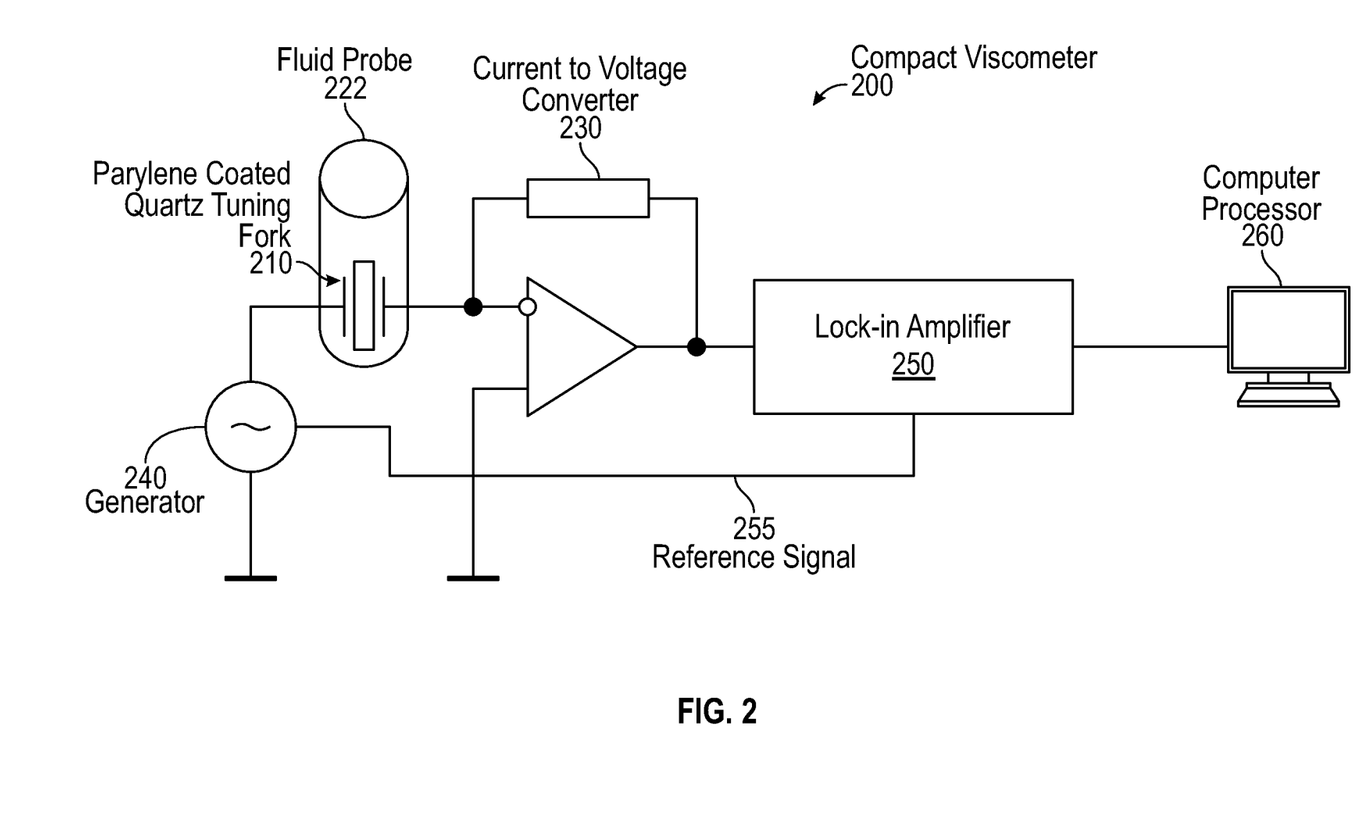
FIG. 2 shows an apparatus in accordance with one or more embodiments.

FIG. 2 depicts, in accordance with one or more embodiments, an electronic circuit of an apparatus to measure the viscosity and density of a fluid. Specifically, FIG. 2 depicts a compact viscometer (200) in accordance with one or more embodiments. The compact viscometer (200) comprises a generator (240), a Parylene coated quartz tuning fork (210), a fluid probe (222), a current to voltage converter (230), a lock-in amplifier (250), and a computer processor (260). The generator (240) may be a signal source, such as a waveform generator, that provides a voltage signal, at one or more frequencies, to actuate the Parylene coated quartz tuning fork (210). In other embodiments, the generator (210) may be a spectrum analyzer with an internal oscillator to both generate and demodulate the voltage signal.

The Parylene coated quartz tuning fork (210) may vibrate when actuated and produce a motion generated piezoelectric current. The current to voltage converter (230) may amplify the piezoelectric current and convert the piezoelectric current to a voltage signal. The lock-in amplifier (250), assisted by a reference signal (255) provided by the generator (240), may demodulate the voltage signal produced by the current to voltage converter (230). The computer processor (260) may read the measurements obtained by the lock-in amplifier (250). The computer processor (260) may be connected to the lock-in amplifier (250) in order to establish a communication protocol. This connection may occur by either a wireless or wired connector such as a general purpose interface bus cable, serial network cable, or universal serial bus cable.

The quartz tuning fork (210) may be coated in Parylene so that it may be deployed in a high-salinity fluid. More specifically, in one or more embodiments, a Parylene conformal film is added throughout the surface area of the quartz tuning fork (210) that is exposed to the fluid. Conventionally, the metallic electrodes deposited on the surface of the quartz crystal are exposed without any dielectric barrier. The Parylene coating prevents the two terminals of the fork to be shorted with each other when immersed in an electrically conductive fluid such as water or brine. Additionally, without being coated in Parylene, the quartz tuning fork (210) may corrode and be inoperable in fluids of high salinity. Those skilled in the art will appreciate that embodiments disclosed herein are not limited to coating the quartz tuning fork (210) using Parylene, and any material that dielectrically insulates the quartz tuning fork (210) may be used without departing from the scope herein. Other coating materials may include silicon nitride, silicon dioxide, or other dielectrics that are deposited via Atomic Layer Deposition or Chemical Vapor Deposition. Other coating processes may include: dip-coating of liquid polymer solutions, such as epoxies, spray coating techniques, or brush coating techniques.

The Parylene coated quartz tuning fork (210) may be installed in a fluid probe (222) that is capable of being immersed in a fluid. The fluid probe (222) may be filled with an epoxy resin to insulate the electrical connections. The fluid probe (222) may feature holes in the side of the housing to avoid the formation of bubbles when immersed in the fluid. The Parylene coated quartz tuning fork (210) vibrates when excited by the voltage signal generated by the generator (240). The resulting vibrations may produce a piezoelectric current. The piezoelectric current may be amplified and converted to a voltage signal by the current to voltage converter (230) and transmitted to the lock-in amplifier (250). The computer processor (260) may read and record one or more vibrational parameters from the output of the lock-in amplifier (250) measured at a single or multiple frequencies. The vibrational parameters are parameters that result from the vibration and piezoelectric current produced by the Parylene coated quartz tuning fork (210) such as resonant angular frequency, current amplitude, and resonance damping parameters. The voltage signal and resulting vibrational parameters transmitted across the electronic circuit of the compact viscometer (200) may be transmitted by using electrical conductors connecting the components.

As shown in FIG. 2, a device based on a fluid probe (222) consisting of a customized quartz tuning fork resonator (210) may be used to obtain the viscosity of high salinity polymer solutions at a specified shear-rate. To determine an accurate value of a fluid property, such as density and viscosity, the compact viscometer (200) may need calibration. This calibration may be a Newtonian calibration. The Newtonian calibration is used to relate the vibrational parameters, created by the vibration of the Parylene coated quartz tuning fork (210), to fluid properties like density and viscosity for Newtonian fluids. This calibration is performed using Newtonian fluids and various transfer functions and hydrodynamic models further outlined in the succeeding paragraphs.

The Newtonian calibration begins by selecting a Newtonian fluid and immersing the fluid probe (222) into the Newtonian fluid. The computer processor (260) controls the frequency at which the Parylene coated quartz tuning fork (210) may be excited. The vibrations of the Parylene coated quartz tuning fork (210) may be excited at a plurality of frequencies controlled by the computer processor (260). The amplitude and phase of the vibrational response from the Parylene coated quartz tuning fork (210) may be relayed by the lock-in amplifier (250) and recorded by the computer processor (260).

Figure 3:
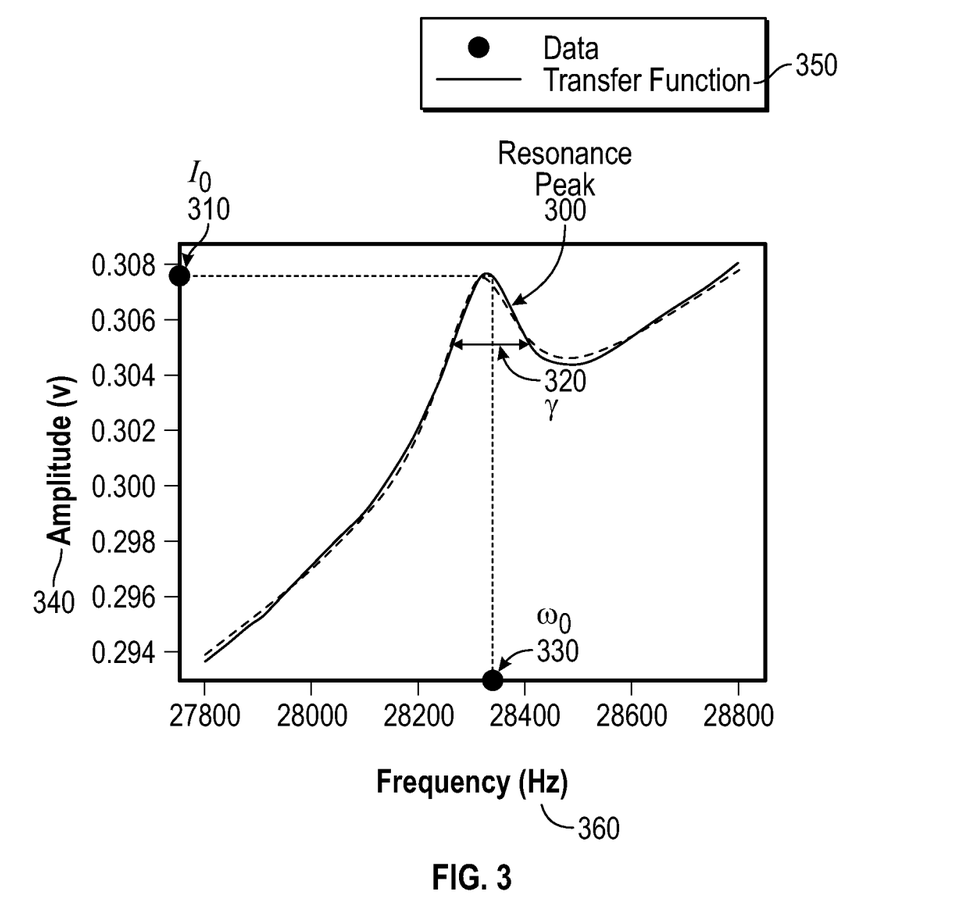
FIG. 3 shows the resonance peak for a Newtonian Fluid on a graph of amplitude plotted against frequency in accordance with one or more embodiments.
Figure 4A:
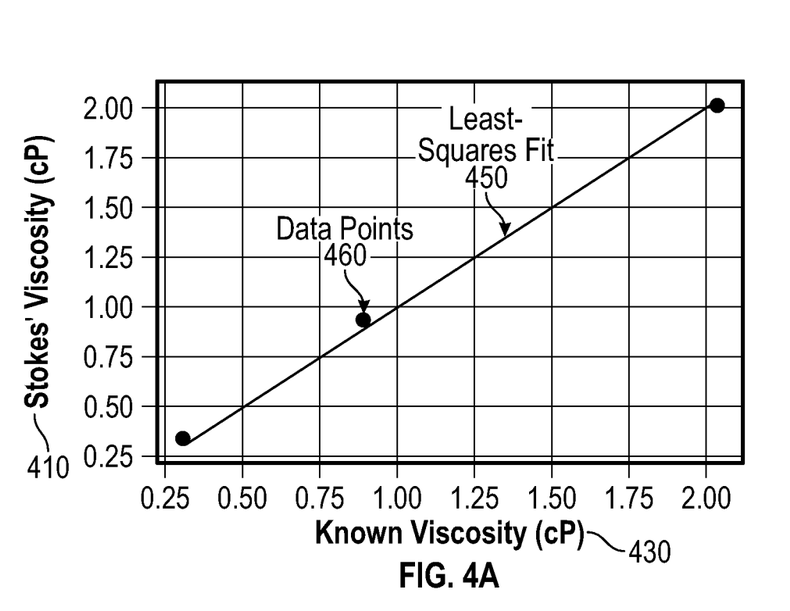
FIG. 4A shows a least-squares fit on a plot of Stokes' viscosity vs known viscosity in accordance with one or more embodiments.
Figure 4B:
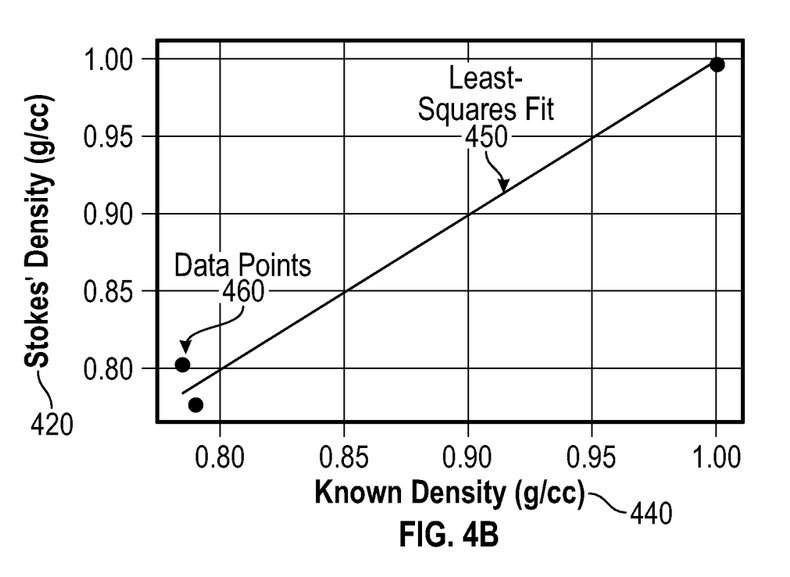
FIG. 4B shows a least-squares fit on a plot of Stokes' density vs known density in accordance with one or more embodiments.

FIGS. 3-4B depict graphs that represent the data used, in one or more embodiments, during the Newtonian calibration of the compact viscometer (200). FIGS. 5-8 depict graphs that represent the data used during the non-Newtonian calibration of the compact viscometer (200). The non-Newtonian calibration uses the results of the Newtonian calibration and further calibrates the compact viscometer (200) to determine the viscosity and density of a non-Newtonian fluid.

FIG. 3 displays the recorded values of the amplitude of vibration (340) of the Parylene coated quartz tuning fork (210) for a plurality of frequencies (360). The y-axis represents the voltage measured by the lock-in amplifier after the current-to-voltage converter. The voltage (V)) may be scaled to the appropriate current (I) depending on the conversion factor, G, used, such that I=GV. A resonance peak (300) is visible as a local maximum in the amplitudes of vibrations (340). The amplitudes of vibrations (340) decrease at greater and lesser frequencies (360) on either side of the resonance frequency (330). In accordance with one or more embodiments, a transfer function (350) may be fit to the recorded values of the amplitude (340) of vibrations. In accordance with one or more embodiments, the transfer function (350) may correspond to a damped force harmonic oscillator transfer function, or a Butterworth-Van Dyke model for an electrical equivalent of a mechanical system transfer function. In accordance with one or more embodiments, the peak current amplitude (310), resonant angular frequency (330), and damping frequency (320) of the resonance peak (300) may be determined. The damping frequency (320) is the frequency half length of the resonance peak (300).

The amplitude of the total current generated, I, may be expressed using the Butterworth-Van Dyke model as shown in equation (1):

$$I = \left(\frac{I_0\omega^2\gamma^2}{\omega^2\gamma^2 + (\omega^2 - \omega_0^2)^2}\right) + i\left(q_0\omega + \frac{I_0\omega\gamma(\omega^2 - \omega_0^2)}{\omega^2\gamma^2 + (\omega^2 - \omega_0^2)^2}\right) \quad \text{Equation (1)}$$

where I=current amplitude, $I_0$=peak current amplitude (310), $\omega$=angular frequency, $\omega_0$=resonant angular frequency (330), and $\gamma$=damping frequency (320). The real and imaginary components of Equation (1) correspond to the in-phase and quadrature components as measured with the lock-in amplifier (250). A linear term in frequency may be added to both in-phase and quadrature components to account for undetermined parasitic components in the signal and phase shifts with respect to the reference signal (255). Equation (1) is used to fit the resonance peak (300) using $\gamma$, $I_0$, $\omega_0$, $q_0$ and any other parameters as fitting parameters.

FIG. 4A shows a graph of two different viscosities in accordance with one or more embodiments. Specifically, FIG. 4A shows a plot of the Stokes' viscosity (410) of a fluid plotted against the known viscosity (430) of the fluid. The Stokes' viscosity (410) is the viscosity of a fluid determined using a Stokes flow hydrodynamic model. The known viscosity (430) is defined as the standard reference viscosity of the fluid. Data points (460) collected from the testing of three Newtonian fluids (acetone, water, and isopropanol) are plotted within the graph of FIG. 4A. The known viscosities (in cP at 20° C.) of acetone, water, and isopropanol are 0.3060, 0.89, and 2.038 respectively.

FIG. 4B similarly shows Stokes' density (420) plotted against the known density (440) of a fluid on a graph. The Stokes' density (420) is the density of the fluid determined using a Stokes flow hydrodynamic model. The known density (440) is defined as the standard reference density of the fluid. Data points (460) collected from the testing of three Newtonian fluids (acetone, water, and isopropanol) are plotted within the graph of FIG. 4B. The known densities (in gr/cc at 20° C.) of acetone, water, and isopropanol are 0.7903, 1.00, and 0.785 respectively. Using the parameters $I_0$, $\gamma$, and $\omega_0$ determined from the transfer function, the damping frequency (320) and the resonant angular frequency (330) may be related to Stokes' viscosity (410) and Stokes' density (420) using the Stokes flow hydrodynamic model shown in equation 2 and 3 (below).

$$\gamma = \frac{1}{2}\frac{CS}{m_{vac}}\left(\frac{f_0}{f_{vac}}\right)^2\sqrt{\frac{\rho\mu f_0}{\pi}} \quad \text{Equation (2)}$$

$$\left(\frac{f_{vac}}{f_0}\right)^2 = 1 + \frac{\beta}{\rho_{obj}}\rho + \frac{B}{\rho_{obj}}\frac{S}{V}\sqrt{\frac{\rho\mu}{\pi f_0}} \qquad \text{Equation (3)}$$

where ρ=density, μ=viscosity. C, B, and β are calibrating parameters that depend on the geometry of the oscillating body in the fluid. S and V are the surface area and volume of a single tuning fork oscillating tine. $m_{vac}$ is the mass of a single tuning fork tine as measured in vacuum or calculated from its geometrical properties and known density of the material, $\rho_{obj} \cdot f_{vac}$ is the resonance frequency as measured in vacuum. $f_0 = \omega_0/2\pi$ and γ are the resonant frequency and damping parameters as obtained from fitting the transfer function in a given fluid.

Both FIG. 4A and FIG. 4B depict a least-squares fit (450). Equations (2) and (3) can be recast as a least-squares fit by writing them in the form Ax=b (and Bx=b), where the matrices A and B are defined below in Equation (4) and (5) for both the density and viscosity. Note that the third term in the right hand side of Equation (2) was omitted. This is due to the fact that this term represents the contribution from the viscous penetration length ($\delta = \sqrt{2\mu/\rho\omega}$) to the added mass, which is a very small value, making this term negligible. The fitting parameters $C_\rho$, and $C_\mu$ are found in the calibration fluids and then used to determine the viscosity and density of unknown fluids. The values $\rho_{ref}$ and $\mu_{ref}$ are the known density (440) and known viscosity (430) values used to calibrate. The least-squares fit (450) may be the result of minimizing a least-squares cost function, shown below in equations 4 and 5, to the difference between the Stokes' viscosity (410) and the known viscosity (430) values, and the difference between the Stokes' density (420) and the known density (440) values.

$$A = \left[\left(\frac{f_{air}}{f_m}\right)^2 - 1\right] \qquad \text{Equation (4)}$$
where
$x = C_\rho; b = \rho_{ref}$ $$B = \frac{\gamma^2 f_{air}^2}{f_m^5 \rho_{ref}} \qquad \text{Equation (5)}$$
where
$x = C_\mu; b = \mu_{ref}$ where $f_{air}$=the frequency of the Parylene coated quartz tuning fork (210) in air, $f_m$=the frequency of the Parylene coated quartz tuning fork (210) in the Newtonian fluid, $C_\rho$ and $C_\mu$ are calibration constants, $\rho_{ref}$=known density (440), and $\mu_{ref}$=known viscosity (430).

These calculations may be done for two or more Newtonian fluids. The Stokes' viscosities (410) and the known viscosities (430) may be plotted in the graph depicted in FIG. 4A with the least squares fit (450) displayed. The Stokes' densities (420) and the known densities (440) may be plotted in the graph depicted in FIG. 4B with the least squares fit (450) displayed. With this least squares fit (450) developed, the Newtonian calibration of the compact viscometer (200) may be completed, and the compact viscometer (200) may be used to find the Newtonian viscosity (503) of any fluid.

Figure 5:
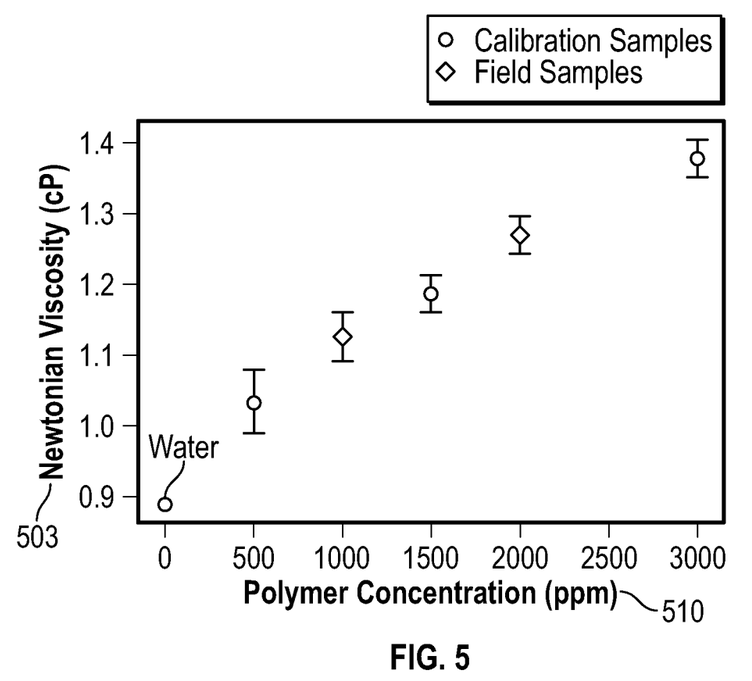
FIG. 5 shows the Newtonian viscosities measured with the compact viscometer at different polymer concentrations in accordance with one or more embodiments.

In order for the compact viscometer (200) to be able to accurately measure fluid properties of a non-Newtonian fluid, it may need to go through a non-Newtonian calibration. The first step of the non-Newtonian calibration may be to prepare two or more, preferably three, non-Newtonian fluids of different polymer concentrations (510). FIG. 5 depicts Newtonian viscosities (503) along the y-axis graphed against the different polymer concentrations (510) of the non-Newtonian fluids being tested. The Newtonian viscosity (503) may be described as the measurement read by the compact viscometer (200) after the Newtonian calibration has been completed. The graph in FIG. 5 plots the Newtonian viscosities (503) and corresponding polymer concentrations (510) of a plurality of non-Newtonian fluids. Herein, the graphs depict three calibration fluids each with polymer concentrations of 500, 1500, and 3000 ppm and two field fluid samples with polymer concentrations of 1000 ppm and 2000 ppm. These 5 non-Newtonian fluids are used in the graphs depicted in FIGS. 5-8.

Figure 6:
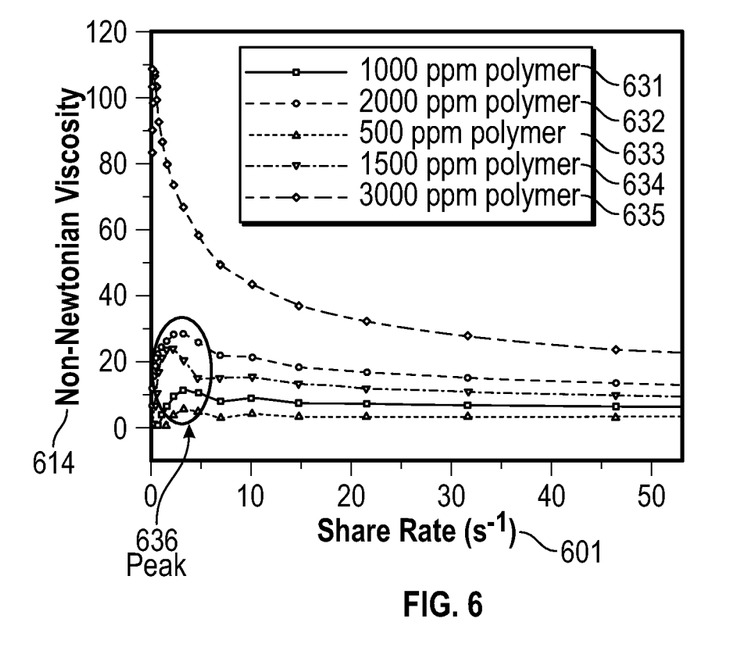
FIG. 6 shows a rheogram plot, generated by a rheometer, for a plurality of fluids in accordance with one or more embodiments.

FIG. 6 depicts a rheogram generated by a laboratory rheometer. This rheogram depicts a plurality of non-Newtonian viscosities (614) measured at a plurality of shear rates (601) for the five non-Newtonian fluids of different polymer concentrations from FIG. 5. A shear rate (601), relative to expected injection rates, may be selected from the rheogram generated by the laboratory rheometer. As shown in FIG. 6, a peak (636) may be observed at low shear rates (601); therefore, the selected shear rate (601) should be a value located after the peak (636) as the shear rate (601) values before the peak (636) may be less reliable. In this embodiment, a shear rate of 6.8 $s^{-1}$ is chosen, and the remainder of the depicted non-Newtonian calibration utilizes the non-Newtonian viscosities (614) at the chosen shear rate of 6.8 $s^{-1}$. The non-Newtonian viscosities at a shear rate (601) of 6.8 $s^{-1}$ for the fluids of polymer concentrations 500 ppm (633), 1500 ppm (634), 3000 ppm (635), 1000 ppm (631), and 2000 ppm (632) are 4.15, 14.9, 49.4, 8.5, and 22.5 cP respectively.

Figure 7:
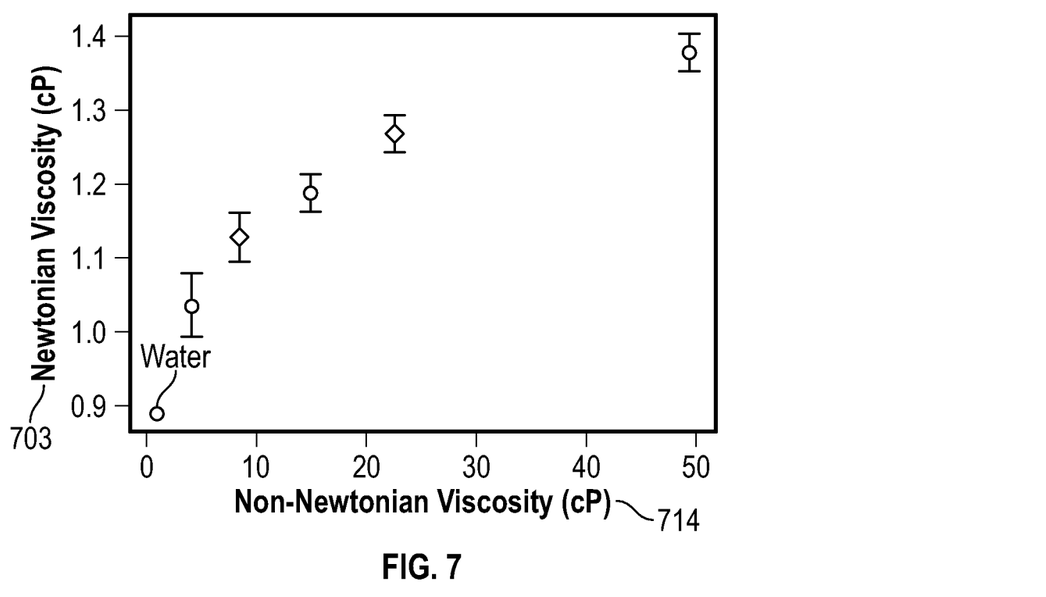
FIG. 7 shows the Newtonian viscosities obtained by the compact viscometer plotted against the non-Newtonian viscosities obtained by the rheometer in accordance with one or more embodiments.

FIG. 7 depicts a calibration plot of the Newtonian viscosities (703) plotted against the non-Newtonian viscosities (714) for the same 5 fluids used in FIGS. 5 and 6. The Newtonian viscosities (703) may again relate to the measurement read by the compact viscometer (200) after the Newtonian calibration has been completed. The non-Newtonian viscosities (714) may again relate to the viscosities generated at the shear rate of 6.8 $s^{-1}$ chosen from the rheogram depicted in FIG. 6. Those skilled in the art will appreciate that embodiments disclosed herein are not limited to obtaining the non-Newtonian viscosity from a rheogram generated by a laboratory rheometer, and any device that is calibrated to measure the viscosity of a non-Newtonian fluid may be used without departing from the scope herein.

Figure 8:
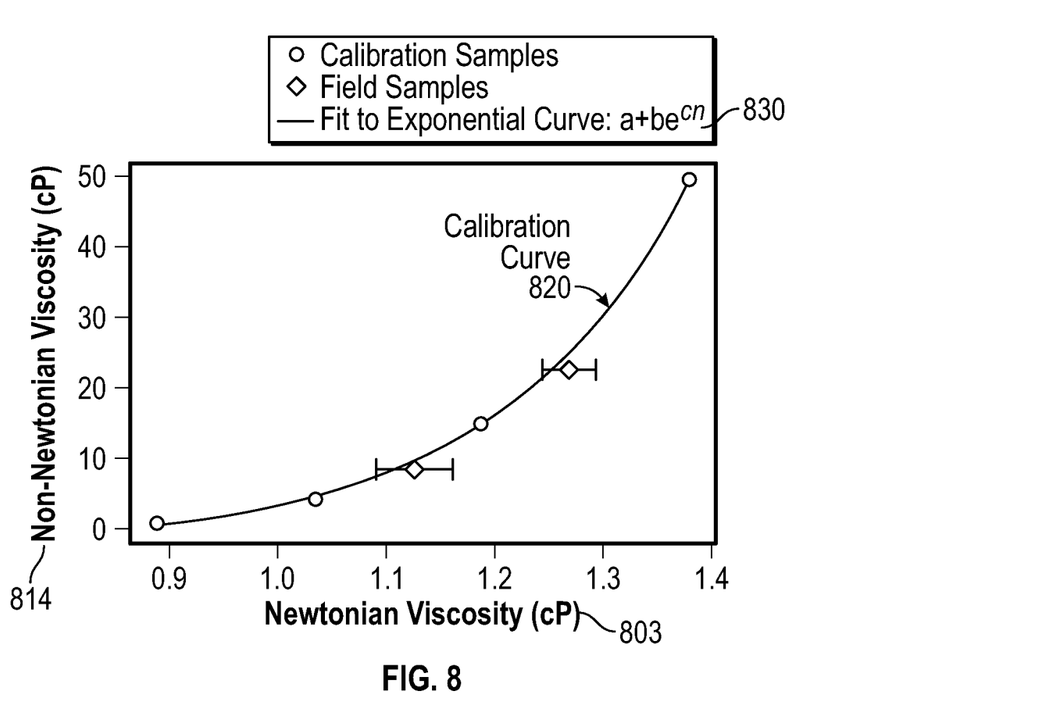
FIG. 8 shows a curve fit to the plot of the Newtonian viscosities obtained by the compact viscometer against the non-Newtonian viscosities obtained by the rheometer in accordance with one or more embodiments.

FIG. 8 depicts the same data points used in FIG. 7 for the same non-Newtonian fluids. A calibration curve (820), may be fit to the data points to mathematically express the relationship between the non-Newtonian viscosity (814) and the Newtonian viscosity (803). In one embodiment, this curve may be determined as an exponential function (830) as in FIG. 8, or it may be a polynomial function of a higher order. Using this calibration curve (820), the non-Newtonian calibration of the compact viscometer (200) may be completed and the compact viscometer may be used to find the non-Newtonian viscosity (814) of any non-Newtonian fluid or the Newtonian viscosity (803) of any Newtonian fluid.

Figure 9A:
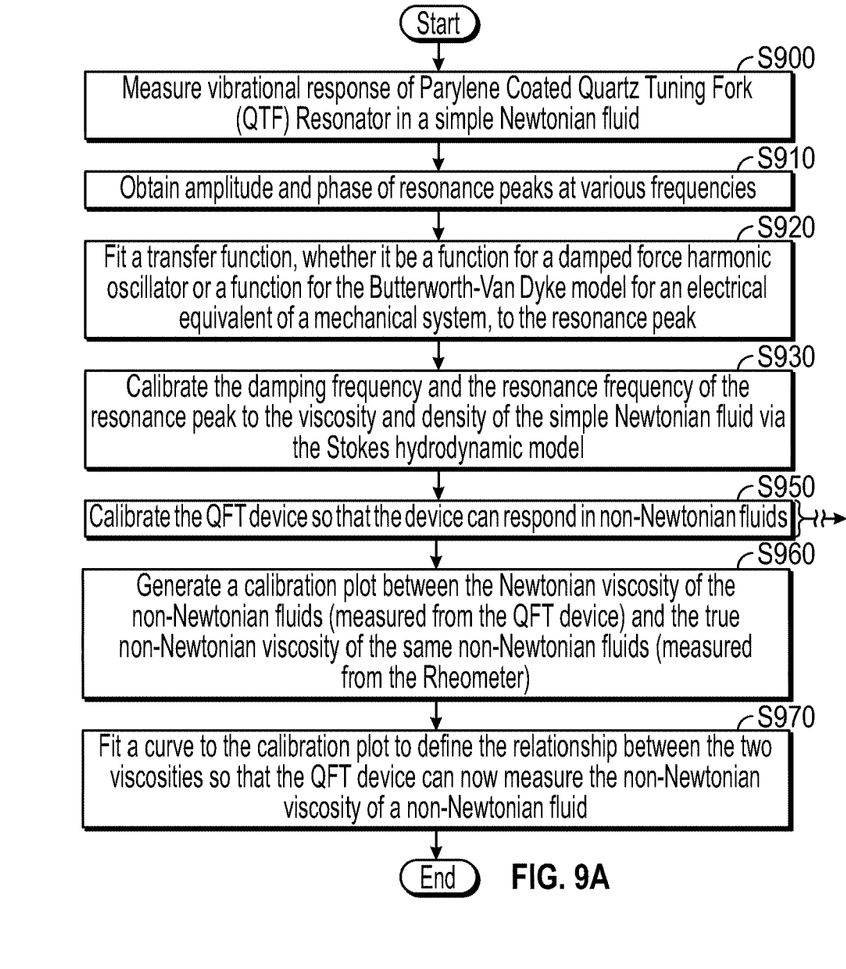
FIG. 9A shows a flowchart in accordance with one or more embodiments.
Figure 9B:
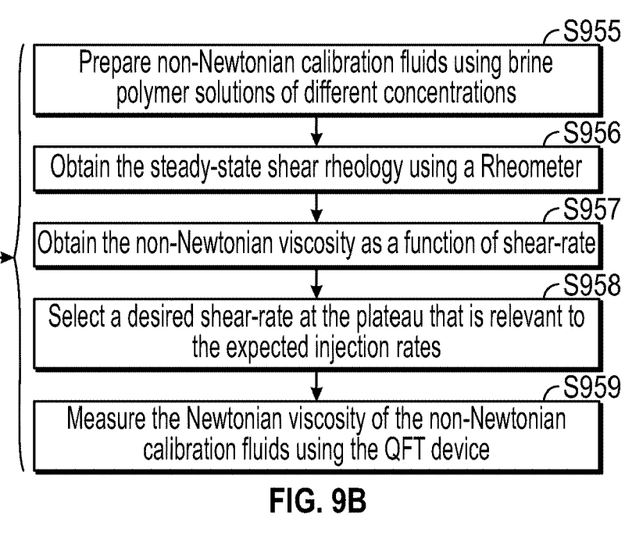
FIG. 9B shows a sub-flowchart of FIG. 8A that depicts how to use the compact viscometer in accordance with one or more embodiments.

FIGS. 9A and 9B depict flowcharts in accordance with one or more embodiments. More specifically, FIGS. 9A and 9B illustrate a method for calibrating the compact viscometer (200) to measure the non-Newtonian viscosity (614, 714, 814) of a non-Newtonian fluid. Further, one or more blocks in FIGS. 9A and 9B may be performed by one or more components as described in FIG. 2 (e.g., computer processor(s) 260). While the various blocks in FIGS. 9A and 9B are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially, the Parylene coated quartz tuning fork (210), installed in a fluid probe (222), may be immersed in a simple Newtonian fluid and actuated by a generator (240). The viscosity ranges of the calibration fluids should be close within a window between the viscosity of water (1 centipoise) up to only a few centipoises. In Step 900, the resulting vibrations of the Parylene coated quartz tuning fork (210) may be recorded and measured by a computer processor (260). The vibrational response is measured using a phase-sensitive method of FIG. 3, or may be measured using any suitable comparable method, such as via an impedance analyzer. In Step 810, the computer processor (260) graphs the vibrational response and determines the amplitude (340) and the phase of a resonance peak (300) at a plurality of frequencies (360). Specifically, the amplitude (340) and phase of the resonance peak (300) at various frequencies (360) are obtained within the bandwidth of a relevant vibrational mode or the resonator. Alternatively, in one or more embodiments, the in-phase and out-of-phase components of the response may also be obtained.

In Step 920, a relevant transfer function (350) may be fit to the determined amplitude (340) and phase at the plurality of frequencies (360). For example, the transfer function (350) may be the Butterworth-Van Dyke transfer function, the damped force harmonic oscillator transfer function, or any other suitable function.

The parameters of the transfer function (350) corresponding to the damping frequency (320) and the resonance frequency (330) are related to Stokes' viscosity (410) and Stokes' density (420) using the Stokes flow hydrodynamic model (Step 930). The compact viscometer (200) is then used to measure the Newtonian viscosity (503, 703, 803) of a Newtonian fluid. At this stage, the compact viscometer (200) may be calibrated to deliver a calibrated non-Newtonian viscosity (614, 714, 814) in non-Newtonian fluids (Step 950). That is, the response of the device is different in the polymer fluids since they are non-Newtonian, so the viscosities and densities measured are shear-rate dependent. The measured viscosity and density is then calibrated to a specific shear-rate as described in FIG. 9B.

Continuing with FIG. 9A, in Step 960, a calibration plot is generated relating the Newtonian viscosity (503, 703, 803) of the non-Newtonian fluids to the non-Newtonian viscosity (614, 714, 814) of the non-Newtonian fluids. A calibration curve (820) is fit to the calibration plot to define the relationship between the Newtonian viscosity (503, 703, 803) and the non-Newtonian viscosity (614, 714, 814) so that the compact viscometer (200) produces the non-Newtonian viscosity (614, 714, 814) of a non-Newtonian fluid (Step 970).

FIG. 9B depicts a flowchart, in accordance with one or more embodiments, for calibrating the compact viscometer (200) for a non-Newtonian fluid. Specifically, FIG. 9B expands on Step 950 of FIG. 9A. In Step 955, at least two, but preferably three or more, non-Newtonian fluids with different polymer concentrations (510), denoted herein "calibration fluids" are prepared. For example, the set of calibration fluids are prepared using brine polymer solutions with different polymer concentrations. A calibrated viscosity measuring device, such as a rheometer, may be used to obtain the steady-state shear rheology of the calibration fluids (Step 956) and obtain the non-Newtonian viscosity (614, 714, 814) as a function of shear-rate (601) (Step 957). The non-Newtonian viscosity (614, 714, 814) as function of shear-rate (601) is obtained between the lowest available shear-rate (601) up to a shear-rate several times higher than ~7 s$^{-1}$. In EOR (100) polymer fluids, 7 s$^{-1}$ is approximately the expected shear-rate (601) while flowing through the formation (110). Step 957 ensures that the selected fluid concentration has a non-Newtonian viscosity (614, 714, 814) that is monotonically decreasing or flat before 7 s$^{-1}$ after the polymer relaxation peak (636) at low shear-rates (601). A shear rate (601) at a convenient location in the rheogram that may be similar to the expected injection rates of the EOR (100) operation is selected (Step 958) and the Newtonian viscosity (503, 703, 803) of the calibration fluids is obtained (Step 959) using the compact viscometer (200).

Figure 10:
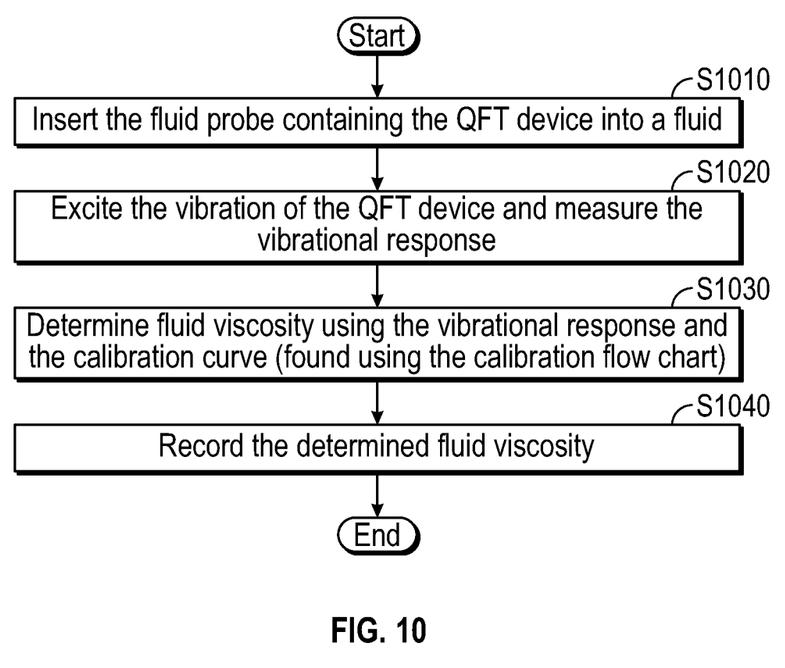
FIG. 10 shows a flowchart in accordance with one or more embodiments.

FIG. 10 shows a flowchart for using the calibrated compact viscometer (200), in accordance with one or more embodiments. Further, one or more blocks in FIG. 10 may be performed by one or more components as described in FIG. 2 (e.g., computer processor(s) 260). While the various blocks in FIG. 10 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In one or more embodiments, the calibrated compact viscometer is used to predict the apparent viscosity at 6.8 s$^{-1}$ (the value at which it was designed to be in the reservoir during injection). Initially, the fluid probe (222) containing the Parylene coated quartz tuning device (210) is immersed in a fluid (Step 1010). The fluid may be non-Newtonian or Newtonian. The fluid may be a water mixed with a polymer. A vibration is excited in the Parylene coated quartz tuning device (210) and the amplitude (340) and phase of the vibrational response is measured (Step 1020) using, for example, a computer processor (260). A viscosity and a density of the fluid in which the fluid probe is immersed may be determined (Step 1030) from the vibrational response, based at least in part on a calibration curve (820) that may be derived by the calibration process described above in FIGS. 9A and 9B. The viscosity and the density of the fluid are recorded (Step 1040). Having accurate values of viscosity and density provides the opportunity for quality assurance and quality control at the wellsite (170) or during the operation.

The calibrated compact viscometer (200), may be used in many different embodiments including, without limitation, a laboratory, a wellsite (170) or deployed downhole. More specifically, the device is configured to be deployed in a portable system to be used at surface in the field to monitor for polymer degradation before injection. The device may also be mounted on a hand-held measurement system for quick and easy monitoring of degradation associated with injected polymer solutions. Furthermore, due to its small size, the device may be deployed in logging tools or untethered logging tools for downhole monitoring of polymer degradation.

Figure 11:
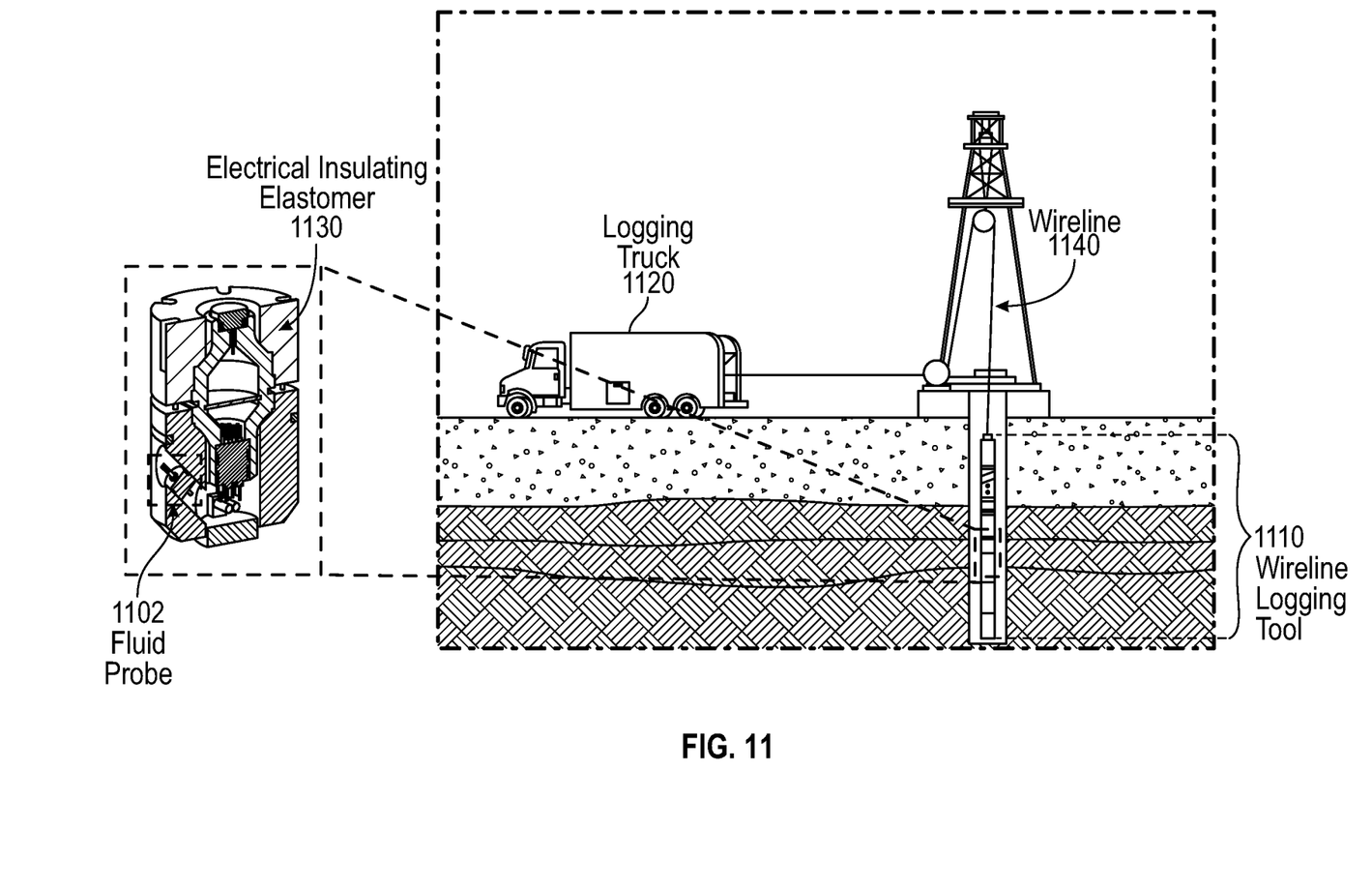
FIG. 11 shows the integration of a fluid probe in a logging tool in accordance with one or more embodiments.

For example, FIG. 11 shows an embodiment of the deployment of the compact viscometer (200). The fluid probe (1102) containing the Parylene coated quartz tuning fork (210) may be encased in an electrical insulating elastomer (1130) to protect the electrical connections and deployed in a wireline logging tool (1110). The electrical signals between the fluid probe and a computer processor (260) at the surface may be transported along the electrically insulated wireline (1140). In accordance with one or more embodiments, this wireline may be connected to a receiver such as a logging truck (1120) which may include a computer processor (260) and a generator (240). The lock-in amplifier (250) and current to voltage converter (230) may be installed in the wireline logging tool (1110). The Parylene coated quartz tuning fork (210), the lock-in amplifier (250), current to voltage converter (230), computer processor (260) and the generator (240) may be installed in a downhole tool unconnected to a wireline (1140).

Those skilled in the art will appreciate that although embodiments disclosed herein employ a Parylene coated quartz tuning fork as the resonator, other resonating devices may be used (such as a micro-electromechanical system or other electromechanical resonators) and other embodiments may be thought of (such as a standard logging tool for downhole deployment, or an electromechanical resonator that can be deployed in-tank during EOR polymer fluid mixing), without departing from the scope of this disclosure.

What is claimed:

1. An apparatus for measuring a viscosity of a non-Newtonian fluid, comprising:
   a Parylene coated quartz tuning fork for immersion in the non-Newtonian fluid;
   an electronic circuit to excite a vibration of the Parylene coated quartz tuning fork and measure one or more vibrational parameters of the Parylene coated quartz tuning fork;
   a computer processor configured to determine a Newtonian viscosity from the vibration of the Parylene coated quartz tuning fork based, at least in part, on a Stokes flow hydrodynamic model; and
   a memory, coupled to the computer processor, and storing a calibration curve configured to convert the Newtonian viscosity to a non-Newtonian viscosity.

2. The apparatus of claim 1, further comprising:
   a fluid probe in which the Parylene coated quartz tuning fork is installed.

3. The apparatus of claim 1,
   wherein the electronic circuit comprises:
      a generator that provides a voltage signal to actuate the Parylene coated quartz tuning fork and provides a reference signal to a lock-in amplifier;
      a converter to convert a current, produced by the Parylene coated quartz tuning fork, to a voltage; and
      the lock-in amplifier to amplify a measured response of the Parylene coated quartz tuning fork using the reference signal from the generator.

4. The apparatus of claim 3,
   wherein the computer processor is operatively connected to the lock-in amplifier by a wired connector that allows a communication protocol to be established,
   wherein the lock-in amplifier is operatively connected to the converter by an electrical conductor and to the Parylene coated quartz tuning fork by an electrical conductor, and
   wherein the converter is operatively connected to the Parylene coated quartz tuning fork by an electrical conductor.

5. The apparatus of claim 3,
   wherein the computer processor is operatively connected to the lock-in amplifier by a wireless connector that allows the communication protocol to be established.

6. The apparatus of claim 1,
   wherein the vibrational parameters further comprise:
      one or more vibrational parameters selected from the group consisting of a resonant angular frequency, a peak current amplitude, and a resonance damping parameter.

7. The apparatus of claim 1,
   wherein the measured non-Newtonian fluid is a high-salinity fluid.

* * * * *